United States Patent [19]

Mather

[11] Patent Number: 5,283,259
[45] Date of Patent: Feb. 1, 1994

[54] METHOD FOR THE PREVENTION OF ECTOPARASITE-MEDIATED PATHOGEN TRANSMISSION

[75] Inventor: Thomas N. Mather, Wakefield, R.I.

[73] Assignee: The President and Fellows of Harvard College, Cambridge, Mass.

[21] Appl. No.: 943,515

[22] Filed: Sep. 11, 1992

[51] Int. Cl.$^5$ ................. A01N 53/00; A01N 65/00
[52] U.S. Cl. ........................... 514/531; 514/65;
514/558; 514/918; 514/919; 424/DIG. 10
[58] Field of Search .............. 424/195.1, DIG. 10;
514/531, 783, 784, 918, 919, 542, 573, 558, 65

[56] References Cited

U.S. PATENT DOCUMENTS 4,707,496  11/1987  Simmons ........................ 514/531

OTHER PUBLICATIONS

Chemical Abstracts (78: 80866K) 1973.
Chemical Abstracts (88: 132037u) 1978.
Chemical Abstracts (104: 226729x) 1986.
Chemical Abstracts (113: 19483h) 1990.
Ciesielski et al., *Anals. New York Acad. Sci.*, 539:283–288 (1988).
Curran et al., *NY Med. Quart.*, 18–21 (1989).
Donahue et al., *Am. J. Trop. Med. Hyg.*, 36:92–96 (1987).
Hanrahan et al., *J. Inf. Dis.*, 150:489–496 (1984).
Mather et al., *Am. J. Trop. Med. Hyg.*, 36:609–614 (1987).
Mather et al., *Annals NY Acad. Sci.*, 539:402–403 (1988).
Piesman et al., *J. Clin. Microbiol.*, 25:557–558 (1987).
Schreck et al., *J. Med. Entomol.*, 23:396–399 (1986).
Yap H. H., *J. Am. Mosq. Cont. Assoc.*, 2:63–67 (1986).
Anon., "New Weapon Against Malaria," *Health & Development (WHO publ.)*, 56:1 (1988).
Anon., *Nat. Res. Couns. Can.*, Publ. No. 24,376 (1986).

Primary Examiner—Frederick E. Waddell
Assistant Examiner—K. Weddington
Attorney, Agent, or Firm—Testa, Hurwitz & Thibeault

[57] ABSTRACT

Disclosed is a method for preventing the transmission of an ectoparasite-borne pathogen to a mammal exposed to predation by the ectoparasite, wherein a time delay exists between attachment of the ectoparasite to the mammal and transmission of the pathogen from the ectoparasite to the mammal. The method comprises applying to the mammal an ectoparacide to kill the ectoparasite in place on the mammal, without necessarily finding or mechanically detaching the ectoparasite, at a time after the exposure of the mammal to the ectoparasite, and within the time delay, thereby preventing transmission of the pathogen from the ectoparasite to the mammal.

10 Claims, No Drawings

METHOD FOR THE PREVENTION OF ECTOPARASITE-MEDIATED PATHOGEN TRANSMISSION

BACKGROUND OF THE INVENTION

This invention relates generally to methods for preventing diseases caused by pathogens transmitted to a mammal by an ectoparasite attached to the mammal.

Current public health measures for preventing the transmission of the Lyme disease spirochete (*Borrelia burgdorferi*) focus around public education and awareness of the tick vector, *Ixodes dammini*. Throughout the northeastern United States, where this serious zoonotic disease is common, the usual recommendations suggest avoiding woody, brushy or grassy vegetation, and performance of self-inspections for ticks following exposure to such tick-bearing habitats. Ciesielski et al., *Ann. NY Acad. Sci.*, 539:283-288 (1988). Insect repellents may help ward off ticks (Schreck et al., *J. Med. Entomol.*, 23:396-399 (1986)), and a product has been designed to suppress transmission by killing ticks as they feed on white-footed mice. Mather et al., *Am. J. Trop. Med. Hyg.*, 36:609-614 (1987); and *Ann. NY Acad. Sci.*, 539:402-403 (1988). Physical removal of embedded ticks within 24 hours also appears to prevent spirochete transmission in animal models. Piesman et al., *J. Clin. Microbiol.*, 25:557-558 (1987).

The prompt removal of ticks requires that the ticks be found, which is not easily accomplished. Statistics show that up to 70% of those patients diagnosed as having Lyme disease reported no history of tick bite. Hanrahan et al., *J. Inf. Dis.*, 150:489-496 (1984); and Curran et al., *NY Med. Quart.*, pp. 18-21, 1989. Thus reliable methods are needed for preventing diseases, such as Lyme disease, which are caused by pathogen transmission by ectoparasites, such as ticks.

An object of the invention is to provide methods which may be used effectively and reliably to prevent ectoparasite-mediated disease transmission, and which may be conveniently and rapidly implemented after or during exposure to areas known or suspected to contain pathogen-bearing ectoparasites.

SUMMARY OF THE INVENTION

The invention provides a method for preventing the transmission of an ectoparasite-borne pathogen to a mammal exposed to predation by the ectoparasite, wherein a time delay exists between attachment of the ectoparasite to the mammal and transmission of the pathogen from the ectoparasite to the mammal. The method comprises applying to the mammal an ectoparacide to kill the ectoparasite in place on the mammal, at a time after the exposure of the mammal to the ectoparasite, and within the time delay, thereby preventing transmission of the pathogen from the ectoparasite to the mammal. Underlying the invention is the surprising discovery that killing the pathogen-bearing ectoparasite attached to the mammal, without necessarily finding or mechanically detaching the ectoparasite, within the interval between attachment and transmission, is effective to stop the transmission.

In one embodiment, wherein a mammal is periodically exposed to predation by an ectoparasite, the application of the ectoparacide to the mammal is repeated within the time delay after each periodic exposure. The ectoparacide comprises a composition capable of killing an attached ectoparasite, before pathogen transmission can occur. The ectoparacide also may comprise a delivery vehicle, such as a cream or a soap. In one embodiment, the ectoparacide may comprise a soap containing a composition capable of killing an attached ectoparasite, such as an insecticide, and the ectoparacide may be applied by washing the mammal with the soap. Soap compositions available in the art may be utilized, such as the pyrethroid-containing insect repellent soap compositions disclosed in Simmons, U.S. Pat. No. 4,707,496 (1987). The method of the invention is advantageous in that it does not rely on either finding or physically removing the ectoparasite.

The method of the invention may be utilized to prevent diseases caused by tick-borne infectious pathogens such as *Borrelia burgdorferi*, *Babesia microti*, *Rickettsia rickettsi*, *R. australis* or *R. tsutsugamushi*. In one embodiment, the method may be utilized to prevent Lyme disease in a mammal, e.g., a human, which is caused by the transmission of the pathogen, *Borrelia burgdorferi*, from the tick, *Ixodes dammini*, to the mammal. In this embodiment, the method comprises applying the ectoparacide to the mammal within approximately 24 hours from the time of exposure of the mammal to the *Ixodes dammini*, to kill the *Ixodes dammini* in place on the mammal, thereby to prevent *Borrelia burgdorferi* transmission and consequently to prevent Lyme disease infection. The ectoparacide may be applied approximately every 24 hours throughout the duration of exposure of the mammal to the *Ixodes dammini*, to prevent *Borrelia burgdorferi* infection. The method of the invention may be utilized conveniently in a wide range of applications for preventing diseases caused by ectoparasite-mediated pathogen transmission to a mammal.

DETAILED DESCRIPTION

The invention provides a method for preventing the transmission of an ectoparasite-borne pathogen to a mammal exposed to predation by the ectoparasite, wherein a time delay exists between attachment of the ectoparasite to the mammal, and transmission of the pathogen from the ectoparasite to the mammal. The method comprises applying to the mammal an ectoparacide to kill the ectoparasite in place on the mammal, without necessarily finding or mechanically detaching the ectoparasite, at a time after the exposure of the mammal to the ectoparasite, and within the time delay, thereby to prevent transmission of the pathogen from the ectoparasite to the mammal. The invention may be utilized in a wide range of applications to prevent a wide range of mammalian diseases caused by the transmission of ectoparasite-borne pathogens, wherein a delay exists between the attachment of the ectoparasite to the mammal and pathogen transmission from the ectoparasite to the mammal.

The ectoparacide comprises a composition which is applied in a sufficient concentration to promptly kill the attached ectoparasite at a time after ectoparasite attachment to the mammal and before pathogen transmission. The ectoparacide also may comprise any of a range of possible delivery vehicles including but not limited to, e.g., a soap or a cream. The ectoparacide may be applied, e.g., directly, or, alternatively, as a spray, or utilizing any of a wide range of possible application methods available in the art. In one embodiment, the ectoparacide may comprise a soap, and may be applied by washing the mammal with the soap. Any of a wide range of possible insecticidal soaps available in the art may be utilized (e.g., U.S. Pat. No. 4,707,496). In one embodiment, the soap conveniently can be rinsed off after just a short period of time. When the mammal is periodically exposed to predation by the ectoparasite, the applying step may be repeated within the time delay after each periodic exposure. The method of the invention successfully prevents pathogen transmission without the necessity of either finding or removing the ectoparasite.

The method of the invention may be utilized in a wide variety of applications to prevent infections, caused by a pathogen transmitted to an individual by an ectoparasite such as, but not limited to, e.g., a tick or a mite. In one embodiment, the transmission of a wide range of infections caused by tick-borne pathogens can be prevented, such as the infections listed in Table 1. Any of a wide range of possible infections caused by ectoparasite-mediated pathogen transmission, wherein a delay exists between the time of ectoparasite attachment and the time of pathogen transmission, may be prevented utilizing the methods of the invention.

TABLE 1

| Infection | Pathogen | Delay |
|---|---|---|
| Lyme disease | Borrelia burgdorferi | 24-36 hr |
| Babesiosis | Babesia microti | 48-54 hr |
| Rocky Mtn. Spotted Fever | Rickettsia rickettsi | 6-8 hr |
| Queensland Tick Typhus | R. australis | 6-8 hr |
| Scrub Typhus | R. tsutsugamushi | 6-8 hr |

In one embodiment, the method of the invention may be utilized to prevent ectoparasite-mediated infections such as Lyme disease, wherein the ectoparasite is the tick, *Ixodes dammini*, and the pathogen is *Borrelia burgdorferi*. The reported time delay between nymphal tick attachment and transmission of the *Borrelia burgdorferi* pathogen is greater than 24 hours. Piesman, et al., *J. Clin. Microbial.*, 25:557-558 (1987). To prevent Lyme disease, the ectoparacide is applied within approximately 24 hours of the time of exposure of the individual to the *Ixodes dammini*, to kill the *Ixodes dammini*, while it is in place on the individual, before *Borrelia burgdorferi* transmission can occur. Utilizing the method of the invention, it is not necessary to either find or mechanically remove the tick. The ectoparacide may be applied periodically approximately every 24 hours throughout the duration of exposure of the individual to the *Ixodes dammini*, to prevent *Borrelia burgdorferi* transmission, thereby preventing Lyme disease. Thus, for example, persons whose leisure activities or jobs involve daily exposure to tick-bearing habitats may, if they wash on a daily basis, by bathing or showering and thoroughly lathering with an ectoparacide-containing soap, be confident that they will not contract Lyme disease.

In one embodiment, the ectoparacide may comprise a composition, capable of killing the ectoparasite in place on the individual, and a delivery vehicle, such as a soap, cream or any other possible vehicle available in the art. Compositions, capable of killing an attached ectoparasite, which may be utilized include e.g., a wide range of insecticides available in the art, such as permethrin or other pyrethroids. In one embodiment, the ectoparacide may comprise a soap containing permethrin, such as the soap described in U.S. Pat. No. 4,707,496, and the ectoparacide may be applied by washing the individual with the soap. Permethrin soaps have been utilized to protect humans from the bites of malarious mosquitoes. Yap H.H., *J. Am. Mosq. Cont. Assoc.*, 2:63-67 (1986).

Anon., "New weapon against malaria". *Health & Development (WHO publ.)*, 56:1 (1988). While insects and other arthropods are extremely sensitive to the action of permethrin, humans and most vertebrates exhibit high levels of tolerance for this insecticide. Anon., *Nat. Res. Couns. Can.*, NRCC Publ. No. 24,376 (1986). Other compositions, capable of killing an attached ectoparasite, which may be utilized include, but are not limited to, e.g., pyrethrums, fatty acids and organophosphate insecticides. Any of a range of possible active ingredients available in the art, capable of killing an attached ectoparasite, may be utilized.

Example 1 illustrates that according to the method of the invention, permethrin may be utilized to prevent Lyme disease infection. In Example 1, washing hamsters within 24 hours after they were infested by *Borrelia burgdorferi*-infected ticks with a soap containing permethrin completely blocked transmission and prevented Lyme disease infection. Thus, the method of the invention may be utilized by individuals who are exposed to a tick-bearing habitat, to prevent Lyme disease infection. The method of the invention is effective regardless of whether an individual is aware of whether they have picked up a tick. The individuals do not have to rely on either finding or removing the tick. The method of the invention may be conveniently utilized throughout the individual's exposure to the tick-bearing habitat.

EXAMPLE 1

Syrian golden hamsters were washed with an insecticidal soap containing 1% permethrin within 24 hours after they were infested by *Borrelia burgdorferi*-infected ticks. *Borrelia burgdorferi* transmission was found to be completely blocked. Eighteen Syrian golden hamsters each were infested with 3-5 *Borrelia burgdorferi*-infected nymphal ticks, and then were washed with either a soap containing 1% permethrin or a non-insecticidal soap (Ivory ™ soap, Proctor and Gamble, Cincinnati, Ohio). Hamsters were anesthetized, wetted under warm running water, thoroughly lathered, held for 1 minute, and then rinsed for 3 minutes. Each hamster was then dried, and placed individually in wire mesh cages over pans of water to collect ticks as they detached.

The nymphal ticks successfully completed engorgement and detached from hamsters washed with Ivory ™ soap, while no engorged ticks were recovered from hamsters washed with permethrin-containing soap. However, unfed, dead ticks were observed remaining attached to the permethrin-washed hamsters, and in the pans of water under these animals. Nine of each of the Ivory ™ soap and permethrin-washed hamsters on which nymphal ticks had attached were then held in separate cages for 3-4 weeks, after which time they were tested for spirochetal infection by tick xenodiagnosis. Donahue et al., *Am. J. Trop. Med. Hyg.*, 36:92-96 (1987). Post-exposure sera were collected at this time, and were compared with sera collected before initial tick exposure for the presence of antibodies against the Lyme spirochete using an immunofluorescent assay. None of the hamsters washed with permethrin-containing soap produced xenopositive ticks, while all of the Ivory ™ soap-washed animals produced at least some xenopositive ticks (Table 2). Furthermore, all of the animals washed with Ivory ™ soap exhibited anti-*Borrelia burgdorferi* antibody titers of $\leq$1:40 (range 1:40–1:320), indicating Lyme spirochete infection, while antibody titers for pre-exposed and permethrin-washed animals were 1:20 or less (Table 2). Thus washing the hamsters with a permethrin-containing soap, to kill the attached ticks within the transmission time delay of 24 hours, completely blocks infection with Lyme spirochetes, even when the infected dead ticks remain attached to the hamsters.

TABLE 2

| Hamsters (9) Washed with | Proportion of Xenodiagnostic Ticks Positive | Frequency of Anti-*B. Burgdorferi* Antibody Titers: | | | | |
|---|---|---|---|---|---|---|
| | | ≦1:20 | 1:40 | 1:80 | 1:160 | 1:320 |
| Permethrin-Containing Soap | 0/170 | 9 | 0 | 0 | 0 | 0 |
| Ivory ™ Soap | 161/170 | 0 | 2 | 3 | 3 | 1 |

These experiments also confirm the observation that Lyme disease spirochete transmission from infected nymphal ticks occurs later than 24 hours following the attachment of infected ticks. Piesman, et al., *J. Clin. Microbiol.*, 25:557–558 (1987). The method of the invention thus allows spirochete transmission to be prevented utilizing a relatively non-toxic insecticidal soap. No toxic effect was observed among hamsters in this study, and the wide-spread human use of this product in WHO-sponsored studies, in the Philippines and elsewhere, would support the absence of toxicity to users. Anon., "New weapon against malaria", *Health & Development* (*WHO publ.*), 56:1 (1988).

Other embodiments are within the following claims.
What is claimed is:

1. A method for preventing the transmission of a tick-borne pathogen to a mammal exposed to predation by a tick infected with said pathogen, wherein a time delay exists between attachment of said infected tick to said mammal and transmission of said pathogen from said infected tick to said mammal, the method comprising:
    applying to said mammal an ectoparacide to kill said infected tick, attached to said mammal, without necessarily finding or mechanically detaching said infected tick, at a time after the exposure of said mammal to said infected tick, and within said time delay, thereby to prevent transmission of said pathogen from said infected tick to said mammal, and
    repeating said applying step within said time delay after each said exposure.

2. The method of claim 1 wherein said ectoparacide comprises a soap, and wherein said applying step comprises washing said mammal with said soap.

3. The method of claim 1 wherein said pathogen is an organism selected from the group consisting of *Borellia burgdorferi*, *Babesia microti*, *Rickettsia rickettsi*, *R. australis* and *R. tsutsugamushi*.

4. The method of claim 1 wherein said tick is *Ixodes dammini*;
    wherein said pathogen is *Borrelia burgdorferi*; and
    wherein said ectoparacide is applied within approximately 24 hours following exposure of said mammal to said tick, *Ixodes dammini*.

5. The method of claim 4, wherein said applying step is repeated periodically approximately every 24 hours throughout the duration of exposure of said mammal to said tick, *Ixodes dammini*.

6. The method of claims 4 or 5 wherein said ectoparacide comprises a soap containing a pyrethroid; and
    wherein said applying step comprises washing said mammal with said soap.

7. The method of claim 6 wherein said pyrethroid is permethrin.

8. The method of claims 4 or 5 wherein said ectoparacide comprises a composition selected from the group consisting of a pyrethrum, an ectoparacidal fatty acid, an ectroparacidal organophosphate insecticide and combinations thereof.

9. The method of claim 1 wherein said ectoparacide comprises a vehicle selected from the group consisting of a cream and a soap.

10. The method of claim 1 wherein said applying step comprises spraying said mammal with said ectoparacide.

* * * * *